United States Patent
Tjioe et al.

(10) Patent No.: US 6,262,261 B1
(45) Date of Patent: Jul. 17, 2001

(54) PROCESS FOR THE PREPARATION OF MELAMINE

(75) Inventors: Tjay T. Tjioe, Sittard (NL); David E. Best, Prairieville, LA (US)

(73) Assignee: DSM NV (NL)

( * ) Notice: Subject to any disclaimer, the term of this patent is extended or adjusted under 35 U.S.C. 154(b) by 0 days.

(21) Appl. No.: 09/545,677

(22) Filed: Apr. 7, 2000

Related U.S. Application Data

(63) Continuation of application No. PCT/NL98/00583, filed on Oct. 12, 1998
(60) Provisional application No. 60/062,574, filed on Oct. 15, 1997.

(51) Int. Cl.$^7$ .................................................. C07D 251/60
(52) U.S. Cl. .............................................................. 544/201
(58) Field of Search ............................................... 544/201

(56) References Cited

U.S. PATENT DOCUMENTS 4,171,091 * 10/1979 Van Hardeveld et al. ............... 294/8
4,465,832 * 8/1984 De Wit et al. ........................ 544/201
4,565,867   1/1986 Thomas et al. ...................... 544/201
5,721,363 * 2/1998 Canzi et al. ......................... 544/201

* cited by examiner

*Primary Examiner*—John M. Ford
*Assistant Examiner*—Venkataraman Balasubramanian
(74) *Attorney, Agent, or Firm*—Pillsbury Winthrop LLP

(57) ABSTRACT

Process for the preparation of melamine from urea via a high-pressure process in which dry melamine powder is obtained by transferring the melamine melt leaving the reactor to a vessel in which the melamine melt is cooled by means of ammonia characterized in that the melamine melt is sprayed into a cooling vessel and cooled by droplets of evaporating liquid ammonia which is sprayed into the same cooling vessel at a pressure above 0.1 MPa and a temperature between 50° C. and the melting point of the melamine in the cooling vessel.

4 Claims, No Drawings

PROCESS FOR THE PREPARATION OF MELAMINE

This application is a con of PCT/NL98/0058 filed Oct. 12, 1998 which claims the benefit of U.S. Provisional Application No. 60/062,574, filed Oct. 15, 1997.

The invention relates to a process for the preparation of melamine from urea via a high-pressure process in which solid melamine is obtained by transferring the melamine melt leaving the reactor to a vessel in which the melamine melt is cooled by means of ammonia.

Such a process is described in, inter alia, U.S. Pat. No. 4,565,867, which describes a high-pressure process for the preparation of melamine from urea. U.S. Pat. No. 4,565,867 in particular describes the pyrolysis of urea in a reactor at a pressure of 10.3 to 17.8 MPa and a temperature of 354 to 427° C. for producing a reaction product. This reaction product contains liquid melamine, $CO_2$ and $NH_3$ and is transferred under pressure, as a mixed stream, to a separator. In this separator, which is kept at virtually the same pressure and temperature as said reactor, said reaction product is separated into a gaseous stream and a liquid stream. The gaseous stream contains $CO_2$ and $NH_3$ off-gases and also melamine vapour. The liquid stream substantially consists of liquid melamine. The gaseous product is transferred to a scrubber unit, while the liquid melamine is transferred to a product cooler. In the scrubber unit the above-mentioned $CO_2$ and $NH_3$ off-gases, which contain melamine vapour, are scrubbed, at virtually the same pressure as the reactor pressure, with molten urea so as to pre-heat the urea and cool said off-gases and remove the melamine that is present from the off-gases. The pre-heated molten urea, which contains said melamine, is then fed to the reactor. In the product cooler the liquid melamine is reduced in pressure and cooled by means of a liquid cooling medium so as to produce a solid melamine product without washing or further purification. In U.S. Pat. No. 4,565,867 use is preferably made of liquid ammonia as liquid cooling medium.

One disadvantage of this method is that in a commercial scale production installation the melamine product that is obtained is nonhomogeneous in both particle size and purity. Important quality parameters include color, reactivity, and the type and concentration of impurities. In the production of melamine for the preparation of melamine based resins, the purity and consistency of the product are very important. Maintaining a low and repeatable level of impurities, for example melem and ammelide, is necessary for the transparency of the melamine based resins.

The aim of the present invention is to obtain an improved high-pressure process for the preparation of melamine from urea in which melamine with a consistent product quality is obtained as a dry powder directly from the liquid melamine melt.

The applicants have now found that melamine powder having the desired product quality powder can be obtained by utilizing a process in which the melamine melt is sprayed into a cooling vessel where it is cooled very rapidly through contact with small droplets of ammonia which are sprayed simultaneously into the same cooling vessel, the cooling vessel having a pressure above 0.1 MPa and a temperature above 50° C. and below the melting point of the melamine. The dry melamine powder produced according to the present process is suitable for applications requiring high purity melamine without the necessity of further purification. The pressure in the cooling vessel is preferably below 20 MPa and more preferably below 15 MPa. The temperature in the cooling vessel is preferably below 270° C. and more preferably below 200° C.

In order to maximize the purity of the solid melamine obtained, it is preferred to cool the melamine melt as fast as possible through rapid and thorough mixing with the cold ammonia sprays. This method solidifies the molten melamine very quickly and thereby prevents the molten melamine from contacting the wall of the cooling vessel. Contact between the molten melamine and the walls of the cooling vessel results in the formation of large lumps of melamine containing different levels of impurities that will limit the purity and consistency of the melamine product that can be obtained.

The applicants have further found that it is necessary to minimize any contact between the liquid ammonia and the walls of the cooling vessel. When the liquid ammonia spray has not been completely evaporated before reaching wall of the cooling vessel, the liquid ammonia itself may trigger the formation of lumps of melamine containing different levels of impurities that will limit the purity and consistency of the melamine product that can be obtained.

In order to minimize the possibility that liquid ammonia will reach the cooling vessel wall, the present process sprays the liquid ammonia into the melamine melt spray as small droplets at a velocity sufficient to provide rapid and thorough mixing of the ammonia and melamine sprays toward the center of the cooling vessel. The small size of the ammonia droplets also increases the rate at which the melamine is cooled by evaporation of the ammonia. In order to obtain the benefits of the rapid cooling provided by the present process, the ammonia sprays should be located near the melamine inlet into the cooling vessel with the spray direction, velocity, and quantity selected to achieve thorough and rapid mixing of the ammonia and melamine sprays to obtain rapid solidification and cooling of the melamine without depositing lumps of melamine on the walls of the cooling vessel. To achieve the mixing of the melamine and ammonia sprays of the present process, it is understood that the ammonia spray nozzles and the melamine inlet will generally be positioned relatively near one another within the cooling vessel.

This need for the close positioning of the ammonia spray nozzles and the melamine inlet is not reflected in the cooling equipment generally used in current state of the art melamine production. In practicing current processes for the cooling of melamine slurries or melts, the nature, location, and rate at which the cooling or drying medium is fed into the cooling vessel is not critical, permitting operation of such processes in vessels having a broad range of physical configurations. In practicing the present process, however, the distance between the melamine inlet and the ammonia spray nozzle vessel becomes important for successful operation. In practice, it is prefered that this distance be less than 2 m, and more preferably, less than 1.5 m, which permits satisfactory operation at reasonable ammonia feed conditions. Greater separation between the melamine inlet and the ammonia spray nozzles would cause an undesirable delay in cooling the melamine, require more extreme ammonia feed conditions, or both.

In practicing the present process, the liquid ammonia spray and the melamine melt spray must be combined at velocities, rates, and directions which are sufficient to produce rapid and thorough mixing of the ammonia and melamine droplets. In order to obtain such mixing, it is preferred that the velocity of the liquid ammonia be at least 6 m/s. This velocity (in m/s) is determined by dividing the volume flow of the liquid (in $m^3/s$) by the smallest cross sectional area for flow (in $m^2$) in the spray nozzle. Similarly, it is preferred that the melamine melt be sprayed at a high velocity.

Although the ammonia spray nozzle(s) may be configured to spray the liquid ammonia in a wide variety of directions, it is preferred that the nozzles be oriented to spray the ammonia droplets directly into the spray of melamine droplets with the central axes of the ammonia nozzles positioned to intersect the central axis of the melamine nozzle. In order minimize the distance the ammonia spray must travel to reach the melamine melt spray, it is preferred to orient the ammonia nozzles such that their central axis are approximately perpendicular to the central axis of the melamine melt nozzle. Measuring along the central axis of the ammonia spray nozzles to the intersection with the central axis of the melamine melt nozzle, this configuration sets the ammonia spray distance equal the separation distance between the nozzles, preferably less than 2 m. It will be understood that the ammonia nozzles may also be oriented to provide an angle of intersection of less than 90 degrees to produce a longer ammonia spray distance, but still preferably less than 5 m, as long as other conditions are selected to ensure the necessary rapid and thorough mixing of the ammonia and melamine melt sprays.

It is preferred to use at least two ammonia spray nozzles to provide satisfactory cooling of the melamine melt. Although there is no theoretical maximum number of ammonia spray nozzles that may be utilized in practicing the present process, it is anticipated that physical and economic considerations will discourage the use of excessive numbers of ammonia spray nozzles. Two such physical considerations are the ability to place the spray nozzles in the cooling vessel without interfering in some way with adjacent spray nozzles and the potential for interaction between the liquid ammonia sprays of adjacent spray nozzles resulting in the formation of larger droplets. Larger ammonia droplets, being less likely to evaporate completely, are more likely to reach the wall of the cooling vessel and produce the negative results mentioned above. In light of these considerations, the applicants believe that in practice the present method would normally operate with fewer than 25 ammonia spray nozzles.

In order to evaluate the nature of the mixing between the melamine melt spray and the ammonia spray, it is helpful to consider the impulse flow value of the ammonia and melamine sprays. The impulse flow value of the ammonia spray would be calculated by multiplying the mass flow through the ammonia nozzle (in kg/s) by the velocity (as calculated above) of the liquid ammonia flow (in m/s) through the ammonia spray nozzles. In the present invention, the impulse value of the ammonia spray is preferably at least 0.1 kg.m/s$^2$ and most preferably at least 0.2 kg.m/s$^2$. Similarly, the impulse flow value of the melamine melt spray is preferably 5 kg.m/s$^2$ and most preferably at least 10 kg.m/s$^2$.

An ammonia spray nozzle suitable for use in the present method has been evaluated (using water at a mass flow equal to that predicted for the liquid ammonia and atmospheric pressure for convenience) and has been found to provide both a droplet size distribution with a $d_{50}$<1.0 mm and pressure drops through the spray nozzle of between 30 KPa and 60 KPa. One type of spray nozzles found to be satisfactory for this purpose are the SK SprayDry® spray nozzles from Spraying Systems Company of Wheaton, Ill.

During the cooling process the droplets from the melamine melt spray are cooled and solidified into melamine powder by contacting the melamine melt spray with a spray of small droplets of liquid ammonia. The volume of liquid ammonia used may be in excess of that necessary for solidification of the melamine melt to provide additional cooling of the solid melamine. To maximize the purity and consistency of the melamine produced, it is preferred that the cooling time (the ammonia spray length (as measured above) divided by the sum of the velocities of the liquid ammonia and melamine melt feeds) be less than 0.04 s, and most preferably below 0.02 s.

The advantage of the method according to the present invention is that melamine powder may be obtained on a commercial scale with a purity greater than 97.5 wt. % and a constant level of several common impurities, i.e. a constant product quality. The purity level and the consistency of impurities makes the melamine sufficient for use in virtually all melamine applications.

In the preparation of melamine, urea is preferably used as starting material in the form of a melt. $NH_3$ and $CO_2$ are byproducts obtained during the melamine preparation, which proceeds according to the following reaction equation:

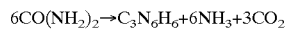

$$6CO(NH_2)_2 \rightarrow C_3N_6H_6 + 6NH_3 + 3CO_2$$

The preparation can be carried out at a high pressure, preferably between 7 and 25 MPa, without the presence of a catalyst. The temperature of the reaction varies between 325 and 450° C. and is preferably between 370 and 440° C. The $NH_3$ and $CO_2$ byproducts are usually returned to an adjoining urea plant.

The above-mentioned aim of the invention is achieved in a plant suitable for the preparation of melamine from urea. A plant suitable for the present invention may comprise a scrubber unit, a reactor in combination with a gas/liquid separator or with a separate gas/liquid separator, optionally a post-reactor, and a cooling and/or expansion vessel.

In an embodiment of the method, melamine is prepared from urea in a plant consisting of a scrubber unit, a melamine reactor, optionally in combination with a gas/liquid separator or a separate gas/liquid separator, optionally a post-reactor, and a cooling vessel. Urea melt from a urea plant is fed to a scrubber unit at a pressure of 7 to 25 MPa, preferably 8 to 20 MPa, and at a temperature above the melting point of urea, preferably between 170–270° C. This scrubber unit may be provided with a jacket so as to provide extra cooling in the scrubber. The scrubber unit may also be provided with internal cooling bodies. In the scrubber unit the liquid urea comes into contact with the reaction gases from the melamine reactor or from a separate gas/liquid separator installed downstream of the reactor or from the post-reactor. In the case of a separate gas/liquid separator, the pressure and temperature may differ from the temperature and pressure in the melamine reactor. The reaction gases substantially consist of $CO_2$ and $NH_3$ and also contain an amount of melamine vapour. The molten urea washes the melamine vapour out of the off-gas and carries this melamine back to the reactor. In the scrubbing process the off-gases are cooled from the temperature of the reactor, i.e from 370–440° C., to 170–270° C., the urea being heated to 170–270° C. The off-gases are removed from the top of the scrubber unit and for instance returned to a urea plant for use as a starting material for the production of urea.

The pre-heated urea is withdrawn from the scrubber unit together with the washed-out melamine and fed, for instance via a high-pressure pump, to the reactor, which has a pressure of 7 to 25 MPa, and preferably of 8 to 20 MPa. Use can also be made of gravity for transferring the urea melt to the melamine reactor by placing the scrubber unit above the reactor.

In the reactor the molten urea is heated to a temperature of 325 to 450° C., preferably of about 370 to 440° C., at a pressure as described above, under which conditions the urea is converted into melamine, $CO_2$ and $NH_3$.

To the reactor an amount of ammonia can be metered, for instance in the form of a liquid or a hot vapor. The ammonia supplied can, for instance, serve to prevent the formation of melamine condensation products such as melam, melem, and melon, or to promote mixing in the reactor. The amount of ammonia fed to the reactor is 0 to 10 mole per mole urea; preferably, 0 to 5 mole ammonia is used, and in particular 0 to 2 mole ammonia per mole urea. The $CO_2$ and $NH_3$ formed in the reaction as well as the extra ammonia supplied collect in the separation section, for instance in the top of the reactor, but a separate gas/liquid separator downstream of the reactor is also possible, and are separated, in gaseous form, from the liquid melamine. The resulting gas mixture is sent to the scrubber unit for removal of melamine vapor and for preheating of the urea melt.

The liquid melamine is withdrawn from the reactor and can be transferred to a post-reactor, in which the liquid melamine melt is brought in contact with ammonia at a temperature between the melting point of melamine and 440° C. The residence time of the melamine melt in the cooling vessel is between two minutes and ten hours, and preferably between ten minutes and five hours. The pressure in the cooling vessel is preferably >5 MPa and in particular between 7 and 25 MPa, this pressure preferably being maintained through introduction of ammonia.

The liquid melamine according to the present invention is then transferred to a cooling vessel where, through cooling with ammonia, solid melamine powder is liberated.

The invention will be elucidated with reference to the following example.

EXAMPLE

Melamine melt having a temperature of 395° C. is introduced, via a spraying device, into a high-pressure vessel and cooled with liquid ammonia which is likewise sprayed into the vessel. The number of spray nozzles used is 4. The ammonia spray nozzles are directed to the direction of the spray cone of the melamine droplets. The distance between the inlet of the liquid ammonia into the cooling vessel and the intersection point of the central axis of the melamine spray cone with the central axis of the ammonia spray cone is 0.5 m. The temperature in the vessel varies between 176 and 182° C. The ammonia pressure in the vessel varies between 6.8 and 9.2 MPa. After 2 minutes the product is cooled further to ambient temperature. The end product contains less than 0.1 wt % of melem and less than 0.05 wt % of ammelide. The product had a consistent quality.

What is claimed is:

1. A method for preparing dry melamine powder from molten melamine comprising the steps of:

producing molten melamine by reacting urea and $NH_3$ in a high-pressure process; spraying said molten melamine into a cooling vessel, said cooling vessel having a temperature between 50° C. and the melting point of melamine and a pressure between 0.1 MPa and 20 MPa; spraying liquid ammonia into said cooling vessel, said liquid ammonia consisting essentially of small droplets of liquid ammonia; mixing said molten melamine spray and said liquid ammonia spray, thereby cooling and solidifying said molten melamine.

2. A method according to claim 1 wherein said small droplets of ammonia have a $d_{50}<1$ mm.

3. A method according to claim 1 wherein said liquid ammonia spray has an impulse flow value of at least 0.1 kg-m/s².

4. A method according to claim 3 wherein said molten melamine spray has an impulse flow value of at least 5 kg-M/s².

* * * * *